United States Patent
Wang et al.

(10) Patent No.: US 9,499,565 B2
(45) Date of Patent: Nov. 22, 2016

(54) COCRYSTAL OF PIPERACILLIN SODIUM AND SULBACTAM SODIUM AND PREPARATION METHOD THEREOF, AS WELL AS PHARMACEUTICAL COMPOSITIONS CONTAINING SAME AND USES THEREOF

(75) Inventors: Haiyong Wang, Beijing (CN); Jing Li, Beijing (CN)

(73) Assignee: BEIJING XINTIANYU TECHNOLOGY DEVELOPMENT CO., LTD., Beijing (CN)

( * ) Notice: Subject to any disclaimer, the term of this patent is extended or adjusted under 35 U.S.C. 154(b) by 0 days.

(21) Appl. No.: 14/428,239

(22) PCT Filed: Sep. 14, 2012

(86) PCT No.: PCT/CN2012/081422
§ 371 (c)(1),
(2), (4) Date: Jun. 24, 2015

(87) PCT Pub. No.: WO2014/040280
PCT Pub. Date: Mar. 20, 2014

(65) Prior Publication Data
US 2015/0299222 A1 Oct. 22, 2015

(51) Int. Cl.
*A61K 31/43* (2006.01)
*A61K 31/496* (2006.01)
*C07D 499/887* (2006.01)
*C07D 499/00* (2006.01)
*C07D 499/04* (2006.01)
*C07D 499/68* (2006.01)

(52) U.S. Cl.
CPC ........... *C07D 499/887* (2013.01); *A61K 31/43* (2013.01); *A61K 31/496* (2013.01); *C07D 499/00* (2013.01); *C07D 499/04* (2013.01); *C07D 499/68* (2013.01)

(58) Field of Classification Search
None
See application file for complete search history.

(56) References Cited

FOREIGN PATENT DOCUMENTS

CN       1167618 A       12/1997

OTHER PUBLICATIONS

Guo, L. (2012). Study on pharmacokinetics and clinical applications of piperacillin sodium/sulbactam sodium injection. *Contemporary Medicine*, 18(5), 74-75.
International Search Report, mailed Jun. 20, 2013 in connection with PCT International Application No. PCT/CN2012/081422, filed Sep. 14, 2012.
Written Opinion of the International Searching Authority, mailed Jun. 20, 2013, in connection with PCT International Application No. PCT/CN2012/081422, filed Sep. 14, 2012.
Notification Concerning Transmittal of International Preliminary Report on Patentability (Chapter I of the Patent Cooperation Treaty), including an International Preliminary Report on Patentability and Written Opinion of the International Searching Authority, mailed Mar. 26, 2015 by the International Bureau of WIPO in connection with PCT International Application No. PCT/CN2012/081422, filed Sep. 14, 2012.

*Primary Examiner* — Samantha Shterengarts
(74) *Attorney, Agent, or Firm* — John P. White; Cooper & Dunham LLP (57) ABSTRACT

Provided in the present invention are a cocrystal of piperacillin sodium and sulbactam sodium and preparation method thereof, as well as pharmaceutical compositions containing the same and uses thereof in treating infections caused by drug-resistant bacteria, such as a "super bacterium" producing NDM-1 and the like. The cocrystal of piperacillin sodium and sulbactam sodium contains diffraction angles of 14.24°, 16.58°, 16.79°, 17.77°, 19.20°, 20.21°, 20.39°, 23.06°, 27.86° and 32.16° represented by $2\theta$ in an X-ray powder diffraction analysis spectrum.

19 Claims, 8 Drawing Sheets

COCRYSTAL OF PIPERACILLIN SODIUM AND SULBACTAM SODIUM AND PREPARATION METHOD THEREOF, AS WELL AS PHARMACEUTICAL COMPOSITIONS CONTAINING SAME AND USES THEREOF

CROSS-REFERENCE TO RELATED APPLICATIONS

This application is a §371 national stage of PCT International Application No. PCT/CN2012/081422, filed Sep. 14, 2012, the contents of which is hereby incorporated by reference in its entirety.

TECHNICAL FIELD

The present invention relates to the cocrystal field of drugs, specifically, to a cocrystal of antibacterial drugs piperacillin sodium and sulbactam sodium and preparation method thereof, as well as pharmaceutical compositions containing same and uses thereof in treating infections caused by drug-resistant bacteria, such as a "super bacterium" producing NDM-1 and the like.

BACKGROUND ART

NDM-1, the acronym of New Delhi metallo-β-lactamase-1, is reported in an article published in a famous English medical magazine—"The Infectious Diseases" on Aug. 11, 2010. The bacteria carrying the gene may produce a special β-lactamase, the active part of the enzyme is metal ion, and it was firstly discovered in the capital of India, New Delhi, so it is named NDM-1. Generally, the NDM-1-producing bacterial are mainly *Escherichia coli* and *Klebsiella pneumonia*, which can cause both nosocomial infection and community infection, including urinary tract infection, bloodstream infection, pneumonia, catheter-related infection, wound infection and so on. Approximately 200 antibiotics on the market in the world have little effect on such new "super bacterium" (FANG Mi, et al. 2011). Therefore, there is an immediate need to find drugs capable of effectively inhibiting infections caused drug-resistant bacteria such as "super bacterium" producing NDM-1, etc.

Piperacillin sodium is semisynthetic penicillin antibiotic, clinically applied to septicemia, upper urinary tract and complicated urinary tract infection, respiratory tract infection, biliary tract infection, abdominal infection, pelvic cavity infection and skin and soft tissue infection etc. induced by sensitive *Enterobacteriaceae* bacteria, *pseudomonas aeruginosa* and *Acinetobacter*. Sulbactam sodium (SBT) is a β-lactamase inhibitor, which is effective against penicillinase produced by drug-resistant *staphylococcus aureus, pneumobacillus* and *Escherichia coli*, and can penetrate cell walls to inhibit β-lactamase produced in cells by bacteria; moreover, SBT itself can also obviously inhibit cephalosporinase produced by *Bacteroides fragilis*, and effectively kill the bacteria of *Acinetobacter* (ZHANG Chunhui, et al, 2004). The combination of piperacillin sodium and sulbactam sodium has good stability, exhibits strong antimicrobial activity against clinically common enzyme-producing bacteria, expands antibacterial spectrum, and has wide application in domestic and foreign markets (SUN Mingjie, et al, 2007).

Crystal form is an important physicochemical property of a drug, and in the aspect of drug quality control, different crystal forms may have different stabilities and thereby affect drug quality. If the crystal form of a drug is fixed, its quality is more stable and is easier to control, otherwise, quality difference may occur between drug batches, such that the stabilities of the drugs differs from each other.

Patent application JP2007099763A discloses two new crystals of piperacillin sodium monohydrate, named type I crystal and type II crystal respectively. The two crystal forms are characterized by having following characteristic diffraction angles (2θ) respectively in PXRD: 3.9°, 4.6°, 5.6°, 6.7°, 9.8° and 7.3°, 7.9°. The patent states that the properties, such as dissolution, moisture absorption, purity, stability, etc. of piperacillin sodium of the two crystal forms are all better than those of amorphous piperacillin sodium.

Wherein, the preparation method of type I crystal comprises: adding certain amount (e.g. 60 g) of piperacillin sodium into certain amount of alcohol aqueous solution (e.g. ethanol 120 ml+water 12 ml), filtering off insoluble substances, sequentially adding certain amount of solvent (e.g. tetrahydrofuran 300 ml), dropping certain amount of acid solution (e.g. acetic acid 6 ml+tetrahydrofuran 60 ml), then stirring at 15-20° C. for 24 h, filtering out the resulted crystal, and washing with alcohol solution (e.g. ethanol+/−other solvent) to obtain the target product with water content of 3.2%.

The preparation method of type II crystal comprises: adding certain amount (e.g. 2 g) of piperacillin sodium into certain amount of alcohol aqueous solution (e.g. ethanol 4 ml+water 1 ml), filtering off insoluble substances, adding certain amount of base (e.g. sodium acetate 0.03 g) and certain amount (12 ml) of ethanol, then stirring at 5° C. for 24 h, filtering out the resulted crystal, and washing with ethanol to obtain the target product with water content of 3.2%.

Patent JP2007246514A discloses two piperacillin sodium crystals, i.e. piperacillin sodium monohydrate and new piperacillin solvate crystal, named type III crystal and type IV crystal respectively. The two crystal forms are characterized by having following characteristic diffraction angles (2θ) respectively in PXRD: 6.1°, 10.2°, 12.4°, 15.6°, 15.8°, 18.6° and 5.3°, 6.1°, 8.7°, 10.2°, 12.4°, 18.6°. The patent shows that compared to amorphous piperacillin sodium, the two crystal forms have good solubility, low moisture absorption and smaller powder volume, easy filtration and drying in industrial production, high purity, and low related substances content.

Wherein, the preparation method of type III crystal comprises: adding certain amount (e.g. 2 g) of piperacillin sodium into certain amount of a mixture solution of ketone, DMF and water (e.g. butanone 2 ml+DMF 3.8 ml+water 0.6 ml), then adding certain amount of ketone again (e.g. butanone 10 ml), filtering off insoluble substances, standing at 5° C. for 24 h, filtering out the resulted crystal, and sequentially washing with certain amount of ketone solution (e.g. butanone 3 ml+DMF 0.9 ml+water 0.1 ml) and certain amount of ketone (e.g. butanone 6 ml) to obtain the target product with water content of 3.2%.

The preparation method of type IV crystal comprises: adding certain amount (e.g. 2 g) of piperacillin sodium into certain amount of mixture solution of dioxane, water and another solvent (e.g. dioxane 6 ml+water 1.2 ml+acetone 13 ml), filtering off insoluble substances, standing at 5° C. for 24 h, filtering out the resulted crystal, and then washing with certain amount of ketone (e.g. acetone 10 ml) to obtain the target product with water content of 3.0% and dioxane content of 7.3%.

Patent application CN200880003783.1 discloses two new piperacillin sodium monohydrate crystal forms, named type V crystal and type VI crystal respectively. The two crystal forms are characterized by having following characteristic diffraction angles (2θ) respectively in PXRD: 3.7°, 5.5°, 7.3°, 11.6°, 14.5°, 18.0° and 5.6°, 7.8°, 12.3°, 15.5°, 17.5°, 23.3°, 24.8°, 28.5°. The patent shows that compared to amorphous piperacillin sodium, the two crystal forms have good solubility, low moisture absorption, easy filtration and drying in industrial production, high purity, and low related substances content.

Wherein, the preparation method of type V crystal comprises: adding certain amount (e.g. 50 g) of type III piperacillin sodium crystal into a pressure vessel (inner diameter of 68 mm, length of 180 mm) equipped with a filter, and under certain temperature (e.g. 40° C.) and certain pressure (e.g. 20 MPa), treating with carbon dioxide mixture at least added with a solvent (e.g. carbon dioxide: methyl acetate=96:4) to obtain the product.

The preparation method of type VI crystal comprises: adding certain amount (e.g. 200 g) of type III piperacillin sodium crystal into a pressure vessel (inner diameter of 68 mm, length of 180 mm) equipped with a filter, and under certain temperature (e.g. 40° C.) and certain pressure (e.g. 40 MPa), treating with pure carbon dioxide for a period of time (e.g. 4 h) to obtain the product.

Furthermore, as to the crystal form of sulbactam sodium, ZHOU Fufu et al. studied the effect of reaction solvents ethyl acetate, acetone, ethanol and methanol on the crystalline state of sulbactam sodium, and discovered by observing with a polarizing microscope that in different solvents, the crystalline states of dry reacted sulbactam sodium products have large difference. When acetone is used as solvent, the crystal of sulbactam sodium is similar to a thin disc body, and has serious dry product agglomeration; when ethyl acetate is used as solvent, the crystal of sulbactam sodium is similar to a cylinder and has large crystal body and good liquidity; when ethanol is used as solvent, the crystal of sulbactam sodium is similar to irregular taper or fan-shaped adhered body and has good liquidity; and when methanol is used as solvent, the crystal of sulbactam sodium is scattered long thin needle-shaped body, and has small bulk density and poor liquidity, wherein the liquidity can be properly improved after ground (Journal of Huaihai Medicine, 2005, 9(23), 423). However, the studies above only provided simple morphology description graph, and there are no systemic comprehensive studies such as powder X-ray diffraction, TG/DSC, etc., i.e. there are no studies performed on the crystal form of sulbactam sodium.

Drug validity period is approved drug service life, representing the time limit capable of ensuring that the drug quality is stable under specified storage conditions. During hospital purchasing process, it is generally required to purchase drugs having a validity period of at least over 1 year; and during storage and pharmacy dispensing processes, the situation that drugs cannot be dispensed for having passed or going to pass the validity period often occurs. The validity periods of respective preparations of current commercial piperacillin sodium and sulbactam sodium are both 24 months. Since antibiotic experiences a long process from production to clinic, including testing, transporting, etc, and clinical dosage of antibiotic is large, problems such as returning and exchanging or difficult selling may easily happen sometimes due to very short drug validity period. If the stabilities of related products of piperacillin sodium and sulbactam sodium can be improved to extend drug validity periods, its economy and safety may certainly be improved. However, although compound preparations of piperacillin sodium and sulbactam sodium have good application value clinically (SUN Mingjie, 2007), there are no studies and reports regarding the crystalline state of the mixture crystal thereof, nor that the product quality is controlled through the crystal form during production processes.

Drug cocrystal is formed by binding active drug ingredients with cocrystal formations in a lattice via non covalent bond such as hydrogen bond, π-π action, Van der Waals' force, etc. It is a new drug in a solid form, and has great application value in pharmaceutics. Compared to simply mixing of two or several drugs, drug cocrystallization can introduce new components without changing the covalent structure of the drug, and greatly improve the stability of compound drugs. Therefore, the study on drug cocrystal is useful for selecting and improving drug therapeutic effect, ensures the stability of content and purity and crystal form consistency of solid raw drugs and preparations thereof during preparation and storage processes, and can extend drug validity period.

The character of commercial piperacillin sodium is white or off-white amorphous powder, so the compound piperacillin sodium-sulbactam sodium using it as raw material (no adjuvants) are also amorphous solid, which ultimately results in that the validity periods of current commercial compound preparations of piperacillin sodium and sulbactam sodium only reach 24 months barely. Thus, industrially, there still is a desire to discover a compound preparation of piperacillin sodium and sulbactam sodium with more stable form, and by improving the stability of compound drugs, the validity period of the drugs is extended, and its economy and safety is certainly improved.

SUMMARY OF THE INVENTION

One purpose of the present invention is to provide a cocrystal of piperacillin sodium and sulbactam sodium. The cocrystal can effectively solve current problems of poor stability and short validity period of compound preparations of piperacillin sodium and sulbactam sodium existing in the prior art.

Another purpose of the present invention is to provide a preparation method for the cocrystal of piperacillin sodium and sulbactam sodium.

Still another purpose of the present invention is to provide pharmaceutical compositions containing the cocrystal of piperacillin sodium and sulbactam sodium and a preparation method thereof.

Yet another purpose of the present invention is to provide uses of the pharmaceutical compositions containing the cocrystal of piperacillin sodium and sulbactam sodium in the preparation of antibacterial drugs.

The cocrystal of piperacillin sodium and sulbactam sodium provided by the present invention comprises diffraction angles of 14.24°, 16.58°, 16.79°, 17.77°, 19.20°, 20.21°, 20.39°, 23.06°, 27.86° and 32.16° represented by 2θ in an X-ray powder diffraction analysis spectrum.

The parameters of the cocrystal of piperacillin sodium and sulbactam sodium provided by the present invention in the X-ray powder diffraction analysis spectrum, viz. interplanar crystal spacing d (Å) and diffraction peak height relative intensity No, are expressed as $d/I/I_0$ and include: 6.21/100.0, 5.34/28.5, 5.27/10.6, 4.98/12.9, 4.61/29.0, 4.39/22.2, 4.35/17.4, 3.85/7.9, 3.20/18.6, and 2.78/8.2.

Specifically, the parameters of the cocrystal in the X-ray powder diffraction analysis spectrum, viz. interplanar crystal spacing d(Å), diffraction peak height relative intensity $I/I_0$ and 2θ, are expressed as $d/I/I_0$ and include: 6.21/100.0/

14.24, 5.34/28.5/16.58, 5.27/10.6/16.79, 4.98/12.9/17.77, 4.61/29.0/19.20, 4.39/22.2/20.21, 4.35/17.4/20.39, 3.85/7.9/23.06, 3.20/18.6/27.85, 2.78/8.2/32.16.

Further, $d/I/I_0/2\theta$ preferably includes: 6.21/100.0/14.24, 5.34/28.5/16.58, 5.27/10.6/16.79, 5.05/4.2/17.53, 4.98/12.9/17.76, 4.83/3.4/18.36, 4.61/29.0/19.20, 4.39/22.2/20.21, 4.35/17.4/20.39, 3.85/7.9/23.06, 3.61/4.0/24.58, 3.56/5.2/24.96, 3.20/18.6/27.85, 3.09/4.5/28.78, 2.90/3.0/30.77, 2.84/4.2/31.42, 2.78/8.2/32.16, 2.66/3.8/33.65, 2.57/2.9/34.85, 2.49/5.8/35.93, 2.34/4.6/38.31, and 2.31/3.8/38.82.

Wherein in a differential scanning calorimetry analysis spectrum, the cocrystal of piperacillin sodium and sulbactam sodium has exothermic peaks at about 192.2° C. and 287.9° C.

Wherein in an infrared absorption spectrum, the cocrystal of piperacillin sodium and sulbactam sodium has absorption peaks at 3437 cm$^{-1}$, 2976 cm$^{-1}$, 1774 cm$^{-1}$, 1715 cm$^{-1}$, 1676 cm$^{-1}$, 1607 cm$^{-1}$, 1520 cm$^{-1}$, 1464 cm$^{-1}$, 1398 cm$^{-1}$, 1304 cm$^{-1}$, 1196 cm$^{-1}$, 1124 cm$^{-1}$, 1090 cm$^{-1}$, 1013 cm$^{-1}$, 949 cm$^{-1}$, 897 cm$^{-1}$, 750 cm$^{-1}$, 704 cm$^{-1}$ and 600 cm$^{-1}$.

Further, the infrared absorption spectrum is obtained by determining via KBr Tabletting method.

In the cocrystal of piperacillin sodium and sulbactam sodium according to the present invention, the molar ratio of piperacillin sodium to sulbactam sodium is 1:1. The preparation method of the cocrystal of piperacillin sodium and sulbactam sodium according to the present invention comprises: adding piperacillin sodium and sulbactam sodium into a mixture solution 1 of ketone, dimethylformamide (DMF) and water, adding ketone 1 and filtering off insoluble substances; then standing at 2-10° C. for 20-30 h, and filtering off resulted crystal; and sequentially washing the filtered crystal with a mixture solution 2 of ketone, dimethylformamide and water and with ketone 2 to obtain the cocrystal.

Wherein, the ketones (ketone in the mixture solutions 1 and 2, and ketone 1, ketone 2) are all selected from one or more of propiophenone, 2-pentanone, butanone and acetone, preferably butanone and/or acetone.

Wherein, the fluctuation of the molar ratio of piperacillin sodium to sulbactam sodium within a certain range has no effect on the quality of the cocrystal A, and the range is 2:1-1:2, preferably 1.5:1-1:1.5, more preferably 1.25:1-1:1.25, and most preferably 1.057:1-1:1.054.

Further, after filtering off the insoluble substances, the temperature for standing is preferably 5° C., and the standing time is preferably 24 h.

Wherein the volume ratio of ketone, dimethylformamide and water in the mixture solution 1 is (40-50):(30-35):12. The volume ratio of ketone, dimethylformamide and water in the mixture solution 2 is (720-800):(60-68):(20-24).

Wherein the mass-to-volume ratio (g:ml) of piperacillin sodium to the total amount of the mixture solution 1 is (40-42):(82-97).

Wherein the mass-to-volume ratio (g:ml) of piperacillin sodium to ketone 1 is (40-42):(280-300).

The pharmaceutical composition containing the cocrystal of piperacillin sodium and sulbactam sodium provided by the present invention comprises 1-100% the cocrystal of piperacillin sodium and sulbactam sodium, preferably 20-100% the cocrystal of piperacillin sodium and sulbactam sodium, and more preferably 50-100% the cocrystal of piperacillin sodium and sulbactam sodium. The percentage (%) here means weight percentage.

Wherein, in addition to the cocrystal, the pharmaceutical composition also comprises 0-80% piperacillin sodium and/or sulbactam sodium, preferably 0-50% piperacillin sodium and/or sulbactam sodium. The addition amount is based on the total weight of the pharmaceutical composition.

In the pharmaceutical composition according to the present invention, the mass ratio of piperacillin sodium to sulbactam sodium is 2:1 (calculated on the base of piperacillin and sulbactam respectively).

The pharmaceutical composition according to the present invention can be prepared into pharmaceutically acceptable formulations, specifically into injection. The injection preferably is powder injection.

The preparation method for the pharmaceutical composition according to the present invention comprises: grinding the cocrystal via a 80 mesh sieve, and mixing under 100-grade sterile room condition to obtain the product; or grinding the cocrystal, adding the ratio of piperacillin sodium and/or sulbactam sodium, and then mixing.

The pharmaceutical composition according to the present invention allows the packing volume difference to be maximally reduced, and effectively reduces the fluctuation of labeling ratio range between them.

The present invention provides uses of the pharmaceutical compositions containing the cocrystal of piperacillin sodium and sulbactam sodium in the preparation of antibacterial drugs.

Further, the present invention provides uses of the pharmaceutical composition of the cocrystal of piperacillin sodium and sulbactam sodium in the preparation of drugs for treating infections caused by drug-resistant bacteria, i.e. the above-mentioned antibacterial drugs mean drugs for treating infections caused by drug-resistant bacteria.

More further, the drug-resistant bacteria mean drug-resistant bacteria such as NDM-1-producing "super bacterium" and the like.

The cocrystal of piperacillin sodium and sulbactam sodium is named as cocrystal A of piperacillin sodium and sulbactam sodium (referred to as "cocrystal A" for short in the text of the present application) in the present invention.

In order to improve the stability of compound piperacillin sodium-sulbactam sodium, the inventors of the present application deeply investigated the existing crystal form studies of piperacillin sodium during the course of studying the compound preparation of piperacillin sodium and sulbactam sodium, and it is showed via repeated studies that: organic acid or organic base is required to be added additionally in the preparation processes of the type I crystal and type II crystal of piperacillin sodium monohydrate, and piperacillin sodium itself is a weak organic base, consequently, considerable amount of piperacillin monohydrate is mixed in the product. Although the physical stability of the product is improved, the product content is not stable, which is not beneficial for clinical use. Furthermore, organic solvent dioxane used in the preparation of type IV crystal is obviously harmful to patient's health. Additionally, the type V crystal and type VI crystal of piperacillin sodium monohydrate adopt supercritical fluid treatment, which significantly increase the difficulty, safety and cost of the product production. Therefore, after comprehensive comparison, the inventors of the present application consider that the type III crystal has medicinal potential, and the preparation conditions thereof are reasonable. However, after a large number of experimental studies, the inventors of the present application surprisingly discovered that: when treating the compound piperacillin sodium-sulbactam sodium with the preparation conditions of type III crystal of piperacillin sodium, the resulted crystal product unexpectedly does not contain the type III crystal of piperacillin sodium and other existing crystal forms of piperacillin sodium, but is a new cocrystal of piperacillin sodium and sulbactam sodium, which can be easily filtered and dried in industrial production and has excellent solubility (>2%), low moisture absorption (<1%), high content (the contents of piperacillin sodium and sulbactam sodium therein are both higher than 96.5% when being placed at room temperature for 28 months), and low related substances content (total content of related substances does not exceed 2% when being placed at room temperature for 28 months). The compound composition/preparation prepared by the cocrystal (named cocrystal A) has obviously improved stability, which not only extends shelf-life of the product, but also further improves safety of the product, reduces the potential harmful risk of drugs and further protects the patient's health.

Typically, during the production process of pharmaceutical composition/preparation, due to the effects of operations such as weighing, mixing and loading, the content of unit preparation is impossible to be consistent with labeled amount. Thus, according to related preparation guide principles, when the content ranges of the active substances in the unit preparation are between 90-110%, it can be considered that the unit preparations have consistent contents thereamong, and are qualified products. Correspondingly, although the compound preparation comprises more than one active substance, the content requirement for each active substance is same. However, as for the compound preparation, although it can be considered that the unit preparations have consistent contents when the content range of every active substance in the unit preparation is between 90-110%, the relative ratio range of the content of each active substance will be enlarged. As for the compound preparation containing two active substances, e.g. a compound preparation having two active substances with labeled ratio of 1:1, according to the above-mentioned principle, it is considered to be qualified generally when the actual ratio range of two active substances therein is 81.8-122.2%. However, the fluctuation range is so wide that drug-sensitive patients are easily subjected to potential damage clinically and the drug effect may be affected. Therefore, there always is a desire to discover a method for effectively reducing the ratio fluctuation range of the active substances in the compound preparation.

However, in the present invention, using the cocrystal of the present invention in the pharmaceutical composition or compound preparation of piperacillin sodium and sulbactam sodium can overcome packing volume deviation. Since the ratio of piperacillin sodium to sulbactam sodium in the cocrystal is fixed, substantially being constantly kept at a mass ratio of about 2:1, when preparing the compound, it avoids problems of large ratio differences among batches, especially potential severe clinical effect-affecting ratio imbalance of sulbactam sodium and piperacillin sodium caused by separately feeding in conventional production, and improves administration accuracy.

Therefore, the cocrystal provided by the present invention is used for treating infections caused by drug-resistant bacteria such as NDM-1-producing "super bacterium" and the like, and has consistent antibacterial activity and stable curative effect; it has excellent solubility, low moisture absorption and smaller powder volume, and the compound composition/preparation prepared therefrom has obviously improved stability, extend shelf-life and validity period of the product, and improved product economy. The use of the cocrystal of the present invention for preparing compound preparation can overcome packing volume deviation, avoid the problem of large ratio differences among batches caused by separately feeding sulbactam sodium and piperacillin sodium in conventional production, and achieve easier quality control; and it can be easily filtered and dried during industrial production, and has high purity and low related substances content. These all further improve product safety, reduce potential harmful risk of drugs, and further protect patient's health.

DESCRIPTION OF DRAWINGS

FIG. 1-$a$ shows an X-ray powder diffraction spectrum (all parts) of the cocrystal A of piperacillin sodium and sulbactam sodium prepared according to example 1, vertical coordinate representing intensity and horizontal coordinate representing 2θ diffraction angle.

FIG. 1-$b$ shows an X-ray powder diffraction spectrum (part of which the 2θ diffraction angle is smaller than 40) of the cocrystal A of piperacillin sodium and sulbactam sodium prepared according to Example 1.

DETAILED DESCRIPTION OF THE PRESENT APPLICATION

The present invention is further described through following examples, but these examples are not intended to limit the protection scope of the present invention.

Experimental operation methods and conditions not specifically described in the present invention are all conventional selections in the art.

BRUKER D8 ADVANCE X ray powder diffractometer is used in the present invention, and determination conditions are: CuK$_\alpha$ radiation, tube voltage: 40 kV, 2θ scanning range: 5-60°, scanning speed: 17.7 s/step, step length: 0.02°. The experimental data of X ray powder diffraction is expressed by interplanar crystal spacing d(Å) and diffraction peak relative intensity I/I$_0$ (e.g. 1% in Table 1 in Example 1), referred to as d/I/I$_0$. Theoretical discussion on X ray powder diffraction spectra can be found in "X-ray diffraction procedures, H. P. Klug and L. E. Alexander, J. Wiley, New York (1974)". German NETZSCH STA409 Comprehensive Thermal Analyzer is used for DSC determination and determination conditions are: heating speed: 10 K/min; flow rate of protection gas $N_2$: 30 mL/min; flow rate of purging gas $N_2$: 20 mL/min; temperature range: 35-300° C. Infrared spectrum is determined using KBr Tabletting method by German Bruker Tensor 27 infrared spectrometer.

All contents and purities in the present invention are determined using high performance liquid chromatography (HPLC), and chromatography conditions are: filler: octadecylsilane chemically bonded silica; mobile phase: 0.005 mol/L tetrabutyl ammonium hydroxide-acetonitrile (70:30) with pH of 5.0 adjusted by acetic acid; flow rate: 1.5 mL per minute; detection wavelength: 230 nm. The number of theoretical plates should not be less than 3500, as calculated according to sulbactam peak, the separation degree of piperazine peak and sulbactam peak should meet the requirements, and before official HPLC determination, the precision, accuracy, linearity and range of each specific to-be-quantified substance are also required to be subjected to methodology validation.

Commercial piperacillin sodium-sulbactam sodium powder injections all have mass ratio of 2:1. "ZHONGJIANSUO" in the present invention means National Institutes for the Control of Pharmaceutical and Biological Products. The unit of temperatures in the present invention is degree centigrade, and additionally, unless otherwise described specifically, the amounts of piperacillin sodium and sulbactam sodium are both calculated based on corresponding piperacillin and sulbactam. The high-purity ketone used in the present invention means that the mass content of ketone is not less than 99%.

EXAMPLE 1

Figure 1A:
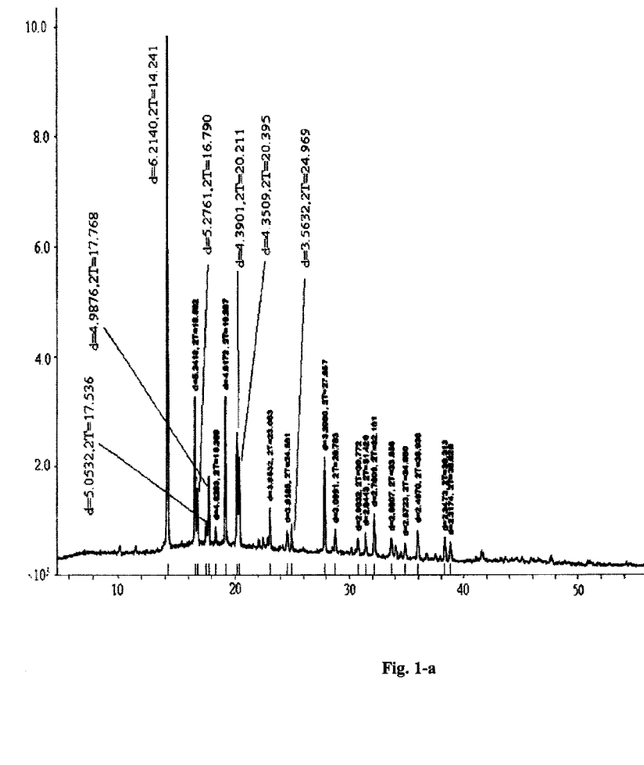
Figure 1B:
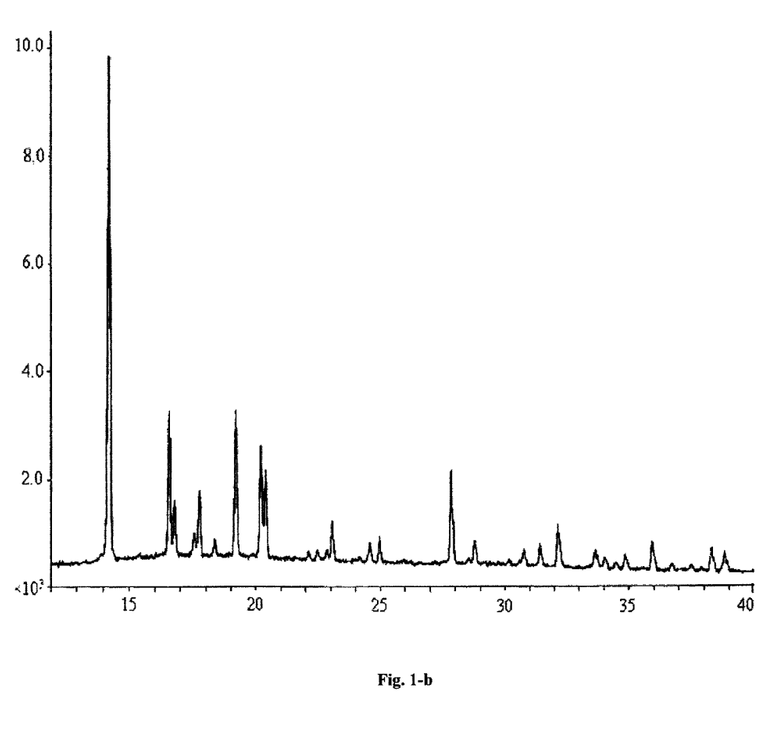
Figure 3:
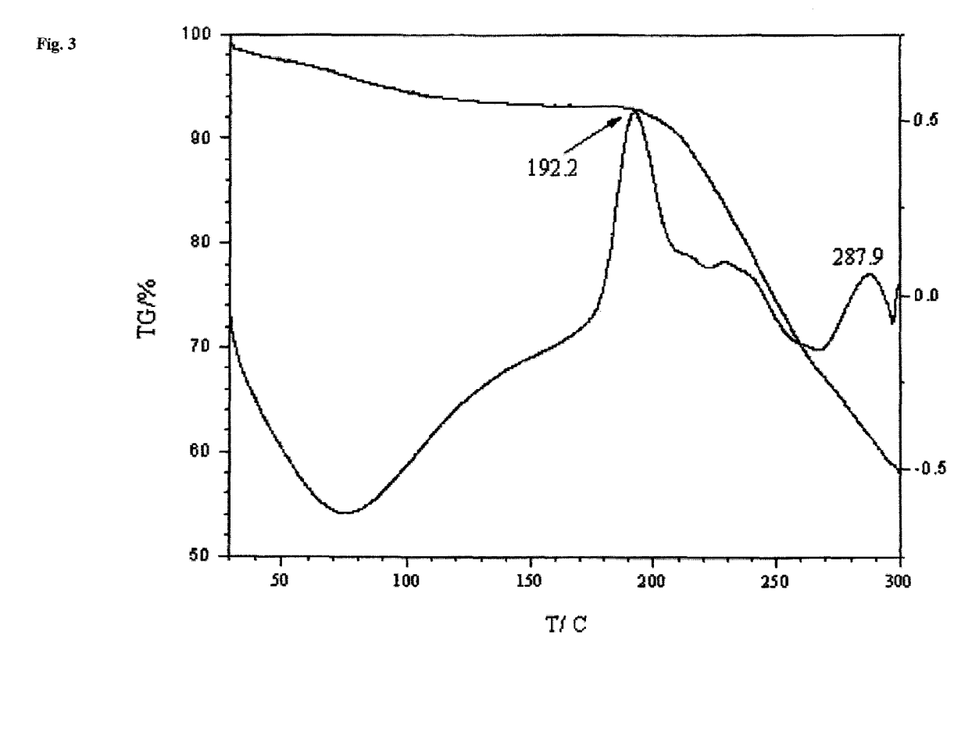
FIG. 3 shows a DSC spectrum of the cocrystal A of piperacillin sodium and sulbactam sodium prepared according to Example 1.
Figure 4:
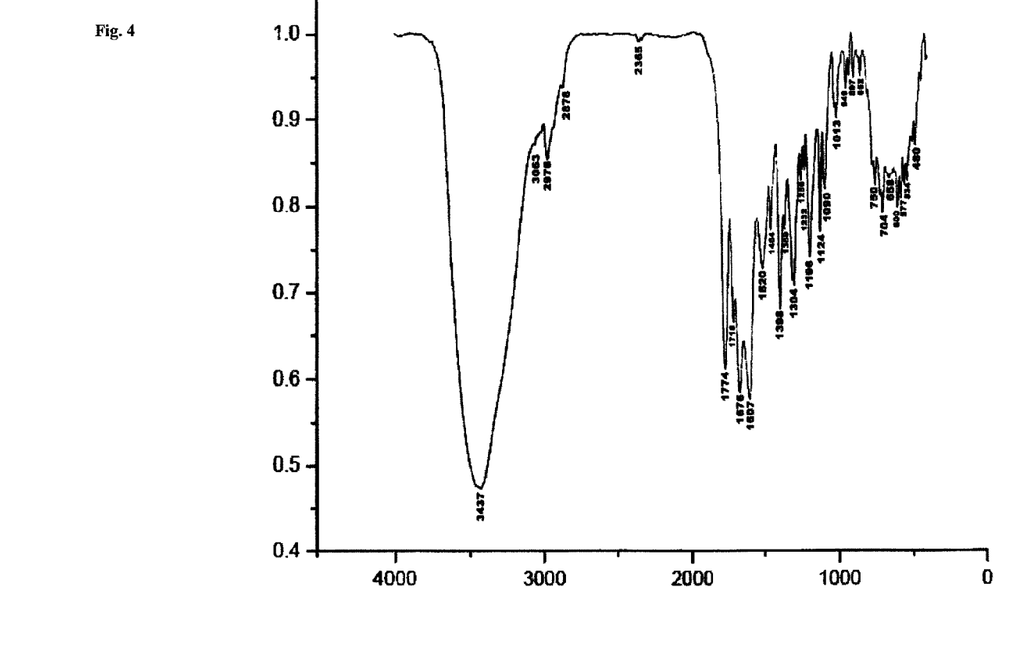
FIG. 4 shows an IR spectrum of the cocrystal A of piperacillin sodium and sulbactam sodium prepared according to Example 1, vertical coordinate representing transmittance and horizontal coordinate representing wave number.

Piperacillin sodium (calculated based on the salt) 40 g (0.074 mol) and sulbactam sodium (calculated based on the salt) 20 g (0.078 mol) were added into a mixture solution of acetone 40 ml+DMF 32 ml+water 12 ml (mixture solution 1), followed by adding acetone 280 ml (high-purity ketone 1), filtering off insoluble substances, standing at 5° C. for 24 h, filtering out resulted crystal, and sequentially washing the above crystal filtered after standing with a mixture solution of acetone 72 ml+DMF 6.8 ml+water 2.4 ml (mixture solution 2) and acetone 120 ml (high-purity ketone 2) to obtain white crystal, i.e. the cocrysal A of piperacillin sodium and sulbactam sodium, of which the X-ray powder diffraction spectrum is shown in FIG. 1-*a* (corresponding data are shown in Table 1, the part whose 2θ diffraction angle is smaller than 40 is shown in FIG. 1-*b*), the DSC spectrum is shown in FIG. 3, and the IR spectrum is shown in FIG. 4.

TABLE 1

X-ray powder diffraction data of the cocrystal A
Scan: 5.0/59.8995/0.0205/1(sec), Cu, 1(max) = 9877
Peak: 13-pts/parabola type filter, threshold value = 3.0, significant figure cutoff point = 0.1%, BG = 3/1.0
Intensity = count, 2T(0) = 0.0(°), wave length spacing = 1.54056 A(Cu/K-alpha1)

| # | 2-Theta | d(A) | BG | Height | I % | Area | $I_1$ % | FWHM |
|---|---------|------|-----|--------|------|--------|---------|-------|
| 1 | 14.241 | 6.2140 | 504 | 9373 | 100.0 | 50823 | 100.0 | 0.089 |
| 2 | 16.582 | 5.3418 | 592 | 2672 | 28.5 | 14637 | 28.8 | 0.090 |

TABLE 1-continued

X-ray powder diffraction data of the cocrystal A
Scan: 5.0/59.8995/0.0205/1(sec), Cu, 1(max) = 9877
Peak: 13-pts/parabola type filter, threshold value = 3.0, significant figure cutoff point = 0.1%, BG = 3/1.0
Intensity = count, 2T(0) = 0.0(°), wave length spacing = 1.54056 A(Cu/K-alpha1)

| # | 2-Theta | d(A) | BG | Height | I % | Area | $I_1$ % | FWHM |
|---|---------|------|-----|--------|------|--------|---------|-------|
| 3 | 16.790 | 5.2761 | 602 | 995 | 10.6 | 5477 | 10.8 | 0.090 |
| 4 | 17.536 | 5.0532 | 590 | 397 | 4.2 | 2074 | 4.1 | 0.086 |
| 5 | 17.768 | 4.9876 | 581 | 1210 | 12.9 | 6927 | 13.6 | 0.094 |
| 6 | 18.368 | 4.8263 | 567 | 322 | 3.4 | 1615 | 3.2 | 0.082 |
| 7 | 19.207 | 4.6172 | 559 | 2717 | 29.0 | 14793 | 29.1 | 0.089 |
| 8 | 20.211 | 4.3901 | 539 | 2084 | 22.2 | 16556 | 32.6 | 0.130 |
| 9 | 20.395 | 4.3509 | 534 | 1634 | 17.4 | 11078 | 21.8 | 0.111 |
| 10 | 23.063 | 3.8532 | 501 | 736 | 7.9 | 3128 | 6.2 | 0.070 |
| 11 | 24.581 | 3.6185 | 451 | 376 | 4.0 | 3432 | 6.8 | 0.150 |
| 12 | 24.969 | 3.5632 | 442 | 485 | 5.2 | 2878 | 5.7 | 0.097 |
| 13 | 27.857 | 3.2000 | 419 | 1740 | 18.6 | 10591 | 20.8 | 0.100 |
| 14 | 28.783 | 3.0991 | 414 | 418 | 4.5 | 3454 | 6.8 | 0.136 |
| 15 | 30.772 | 2.9032 | 394 | 282 | 3.0 | 1897 | 3.7 | 0.110 |
| 16 | 31.426 | 2.8443 | 385 | 393 | 4.2 | 1996 | 3.9 | 0.083 |
| 17 | 32.161 | 2.7809 | 356 | 772 | 8.2 | 5395 | 10.6 | 0.115 |
| 18 | 33.656 | 2.6607 | 322 | 356 | 3.8 | 3777 | 7.4 | 0.174 |
| 19 | 34.850 | 2.5723 | 309 | 273 | 2.9 | 1764 | 3.5 | 0.106 |
| 20 | 35.936 | 2.4970 | 287 | 539 | 5.8 | 4102 | 8.1 | 0.125 |
| 21 | 38.313 | 2.3473 | 260 | 427 | 4.6 | 3390 | 6.7 | 0.130 |
| 22 | 38.828 | 2.3174 | 252 | 355 | 3.8 | 2928 | 5.8 | 0.135 |

EXAMPLE 2

Piperacillin sodium (calculated based on the salt) 400 g (0.74 mol) and sulbactam sodium (calculated based on the salt) 179 g (0.70 mol) were added into a mixture solution of acetone 400 ml+DMF 300 ml+water 120 ml (mixture solution 1), followed by adding acetone 2800 ml (high-purity ketone 1), filtering off insoluble substances, standing at 5° C. for 24 h, filtering out resulted crystal, and sequentially washing the above crystal filtered after standing with a mixture solution of acetone 700 ml+DMF 60 ml+water 20 ml (mixture solution 2) and acetone 1200 ml (high-purity ketone 2) to obtain white crystal, i.e. the cocrysal A of piperacillin sodium and sulbactam sodium, of which the X-ray powder diffraction spectrum, DSC spectrum and IR spectrum are similar to FIGS. 1, 3 and 4 respectively, showing that the prepared crystal is cocrystal A.

EXAMPLE 3

Piperacillin sodium (calculated based on the salt) 420 g (0.78 mol) and sulbactam sodium (calculated based on the salt) 200 g (0.78 mol) were added into a mixture solution of acetone 500 ml+DMF 350 ml+water 120 ml (mixture solution 1), followed by adding acetone 3000 ml (high-purity ketone 1), filtering off insoluble substances, standing at 5° C. for 24 h, filtering out resulted crystal, and sequentially washing the above crystal filtered after standing with a mixture solution of acetone 800 ml+DMF 60 ml+water 20 ml (mixture solution 2) and acetone 1400 ml (high-purity ketone 2) to obtain white crystal, i.e. the cocrysal A of piperacillin sodium and sulbactam sodium, of which the X-ray powder diffraction spectrum, DSC spectrum and IR spectrum are similar to FIGS. 1, 3 and 4 respectively, showing that the prepared crystal is cocrystal A.

EXAMPLE 4

Figure 2:
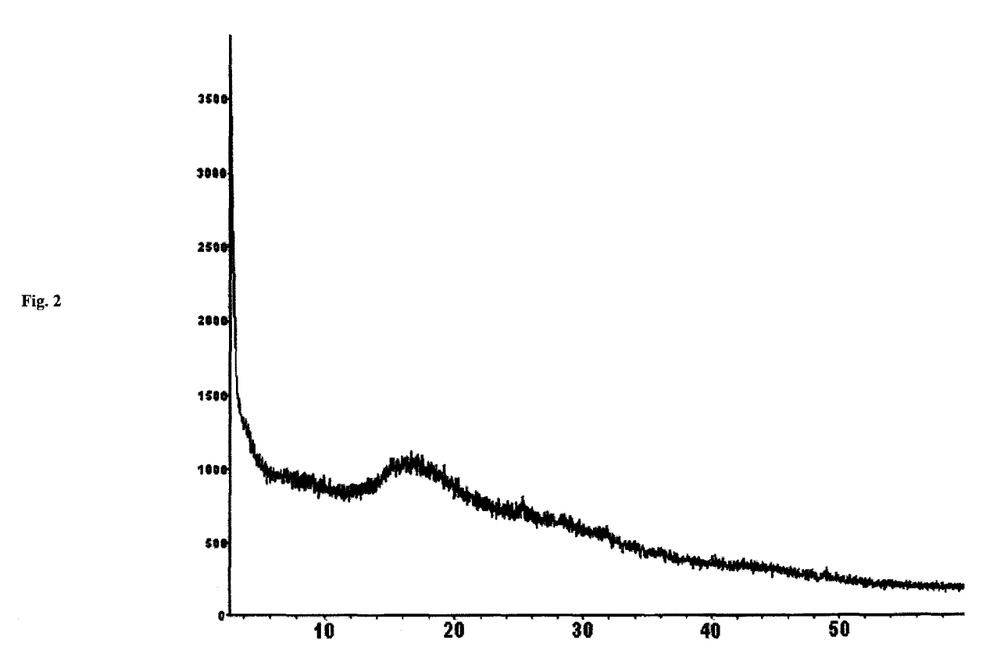
FIG. 2 shows an X-ray powder diffraction spectrum of commercial piperacillin sodium-sulbactam sodium powder injection (mass ratio of 2:1, amorphous) determined according to Example 4, vertical coordinate representing intensity and horizontal coordinate representing 2θ diffraction angle.
Figure 5:
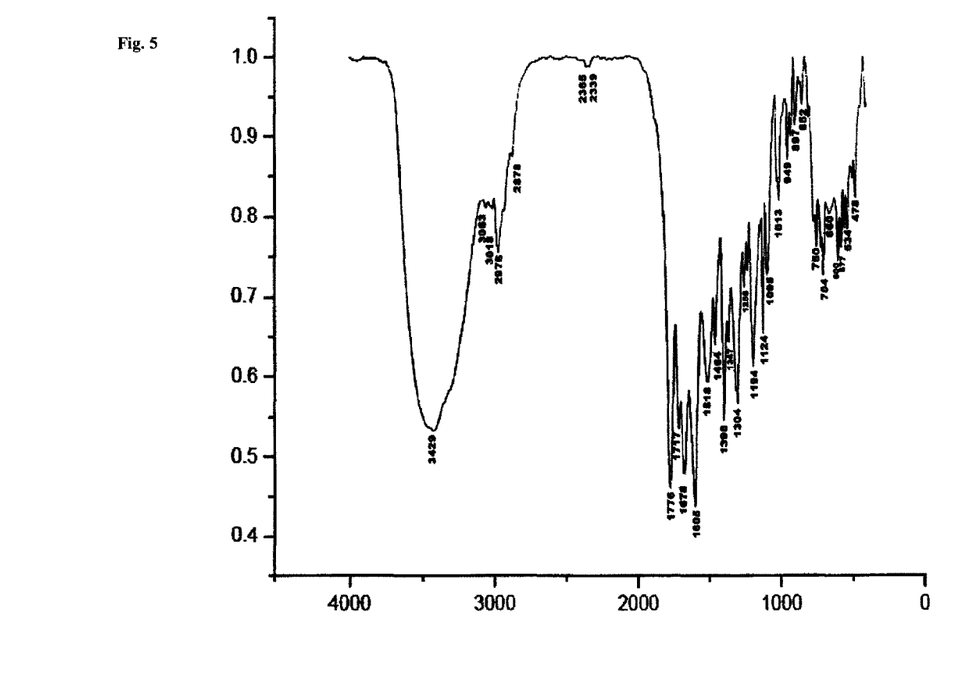
FIG. 5 shows an IR spectrum of commercial piperacillin sodium-sulbactam sodium powder injection (mass ratio of 2:1, amorphous) determined according to Example 4, vertical coordinate representing transmittance and horizontal coordinate representing wave number.
Figure 6:
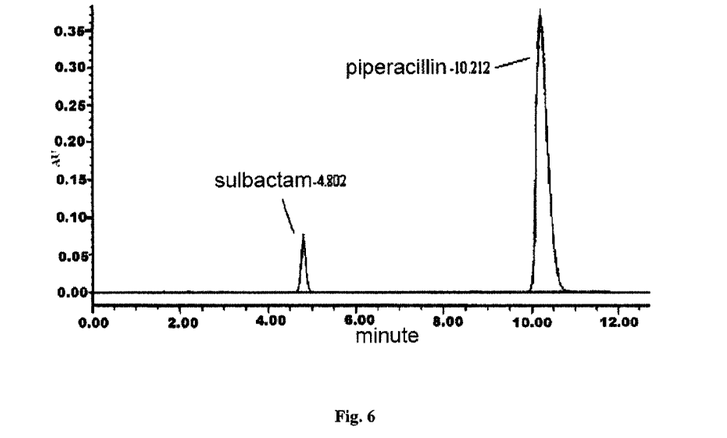
FIG. 6 shows a HPLC spectrum of the cocrystal A of piperacillin sodium and sulbactam sodium prepared according to Example 1.
Figure 7:
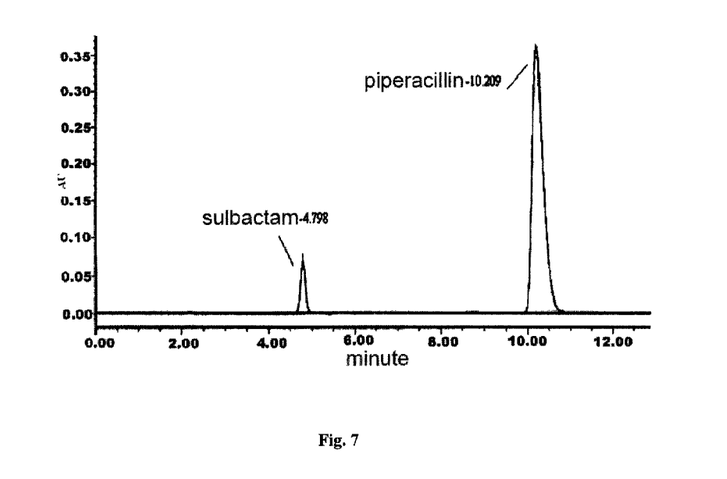
FIG. 7 shows a HPLC spectrum of the cocrystal A of piperacillin sodium and sulbactam sodium prepared according to Example 2.
Figure 8:
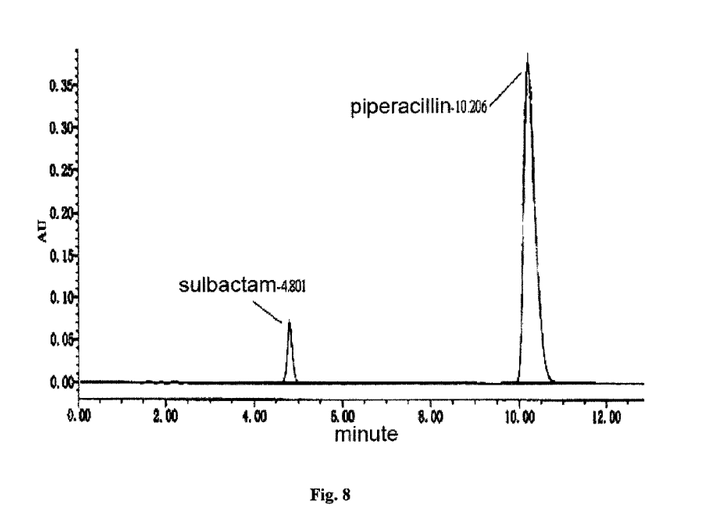
FIG. 8 shows a HPLC spectrum of the cocrystal A of piperacillin sodium and sulbactam sodium prepared according to Example 3.
Figure 9:
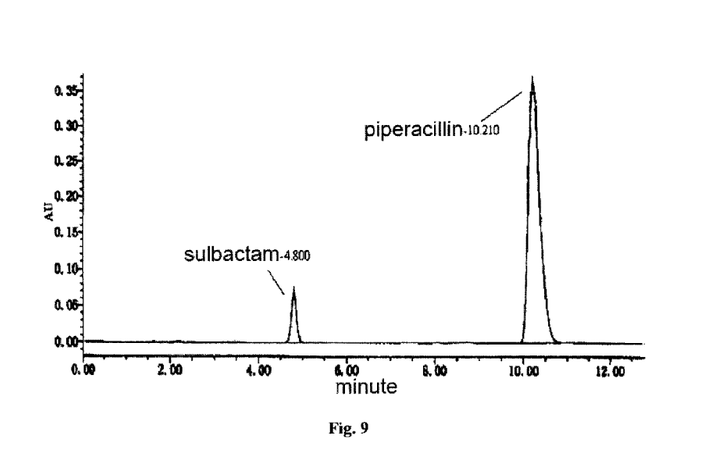
FIG. 9 shows a HPLC spectrum of mixed piperacillin sodium reference and sulbactam sodium reference provided by ZHONGJIANSUO at molar ratio of 1:1 (calculated by piperacillin and sulbactam respectively) determined according to Example 5.

The crystal form of commercial piperacillin sodium-sulbactam sodium powder injection (2:1) was determined, and the X-ray powder diffraction spectrum thereof is shown in FIG. 2. The infrared spectrum of the commercial piperacillin sodium-sulbactam sodium powder injection was determined using KBr Tabletting method, and the IR thereof is shown in FIG. 5.

EXAMPLE 5

Reference Piperacillin sodium and reference sulbactam sodium provided by ZHONGJIANSUO were mixed at a molar ratio of 1:1 (calculated based on the salt, precisely weighing 53.9 mg and 25.5 mg respectively) and used as external standard (mixed sample), then the contents of piperacillin sodium and sulbactam sodium in the cocrystal A of piperacillin sodium and sulbactam sodium were determined by high performance liquid chromatography.

The method for determination comprises: precisely weighing 100 mg of samples of Example 1, Example 2, Example 3 and external standard respectively (calculated based on the actual weight), adding mobile phase for dissolving and diluting into 1 ml of solution containing 1 mg of to-be-determined sample, precisely collecting 10 μl, injecting into the chromatograph, and calculating the contents of $C_{23}H_{27}N_5O_7S$ and $C_8H_{11}NO_5S$ in each tested sample by peak area according to external standard method. Per milligram of samples of Examples 1-3 comprise piperacillin sodium/sulbactam sodium 679 ug/321 ug, 675 ug/325 ug and 680 ug/320 ug (calculated based on the salt), respectively, and the molar ratios of piperacillin sodium to sulbactam sodium are 0.999, 1.020 and 0.994, respectively (calculated by salt). The HPLC spectra are shown in FIGS. 6-9 respectively, and the corresponding peak results are also shown in Tables 2-5.

TABLE 2

HPLC peak results of the cocrystal A prepared according to Example 1

| Number | Name | Retention time | Area (mV * s) | Height (mV) | USP Separation degree | USP theoretical tower plate number | USP trailing |
|---|---|---|---|---|---|---|---|
| 1 | Sulbactam | 4.802 | 570687 | 69116 | | 7585.101 | 1.039 |
| 2 | Piperacillin | 10.212 | 6618632 | 367246 | 14.956 | 6941.741 | 1.488 |

TABLE 3

HPLC peak results of the cocrystal A prepared according to Example 2

| Number | Name | Retention time | Area (mV * s) | Height (mV) | USP Separation degree | USP theoretical tower plate number | USP trailing |
|---|---|---|---|---|---|---|---|
| 1 | Sulbactam | 4.798 | 573376 | 69263 | | 7557.222 | 1.041 |
| 2 | Piperacillin | 10.209 | 6514093 | 362468 | 14.963 | 6966.025 | 1.483 |

TABLE 4

HPLC peak results of the cocrystal A prepared according to Example 3

| Number | Name | Retention time | Area (mV * s) | Height (mV) | USP Separation degree | USP theoretical tower plate number | USP trailing |
|---|---|---|---|---|---|---|---|
| 1 | Sulbactam | 4.801 | 584629 | 70955 | | 7623.588 | 1.038 |
| 2 | Piperacillin | 10.206 | 6817938 | 378007 | 14.924 | 6900.812 | 1.503 |

TABLE 5

HPLC peak results of the mixed sample provided by ZHONGJIANSUO

| Number | Name | Retention time | Area (mV * s) | Height (mV) | USP Separation degree | USP theoretical tower plate number | USP trailing |
|---|---|---|---|---|---|---|---|
| 1 | Sulbactam | 4.800 | 565675 | 68481 | | 7600.944 | 1.040 |
| 2 | Piperacillin | 10.210 | 6555252 | 364598 | 14.977 | 6973.506 | 1.486 |

The above-mentioned determination results shows that the cocrystal A of Examples 1-3 of the present invention comprises piperacillin sodium and sulbactam sodium at a determined molar ratio, and the molar ratio of them is 1 (very close).

The cocrystal A of the present invention is an independent product, which can be independently used for preparing compound preparation, and also preparing the compound preparation after mixing with some ingredient in the cocrystal. They both can meet the provisions of national drug standard, as shown in following Examples 6-9.

EXAMPLE 6

Preparation of Powder Injection with Piperacillin Sodium:Sulbactam Sodium at a Mass Ratio of 2:1

Formulation 1: 3000 g of the cocrystal A of piperacillin sodium and sulbactam sodium were prepared into 1000 units of powder injection.

The preparation method comprises: grinding the cocrystal A of piperacillin sodium and sulbactam sodium via a 80 mesh sieve, under 100-grade sterile room condition, mixing well by adopting a multi-direction moving mixer, subpackaging via a subpackaging machine according to 3.0 g per bottle, capping, labellling, and packaging to obtain sterile piperacillin sodium-sulbactam sodium powder injection for injection with mass ratio of 2:1 (calculated based on piperacillin and sulbactam), meeting national drug standard.

EXAMPLE 7

Preparation of Powder Injection with Piperacillin Sodium:Sulbactam Sodium at a Mass Ratio of 2:1

Formulation 2: 727.5 g of the cocrystal A of piperacillin sodium and sulbactam sodium and 22.5 g sulbactam sodium were prepared into 1000 units of powder injection.

The preparation method comprises: grinding the cocrystal A of piperacillin sodium and sulbactam sodium via a 80 mesh sieve, under 100-grade sterile room condition, adding sulbactam sodium, mixing well by adopting a multi-direction moving mixer, subpackaging via a subpackaging machine according to 0.75 g per bottle, capping, labellling, and packaging to obtain sterile piperacillin sodium-sulbactam sodium powder injection for injection with mass ratio of 2:1 (calculated based on piperacillin and sulbactam), meeting national drug standard.

EXAMPLE 8

Preparation of Powder Injection with Piperacillin Sodium:Sulbactam Sodium at a Mass Ratio of 2:1

Formulation 3: 750 g of the cocrystal A of piperacillin sodium and sulbactam sodium, 265 g sulbactam sodium and 485 g piperacillin sodium, were prepared into 1000 units of powder injection.

The preparation method comprises: grinding the cocrystal A of piperacillin sodium and sulbactam sodium via a 80 mesh sieve, under 100-grade sterile room condition, adding sulbactam sodium and piperacillin sodium, mixing well by adopting a multi-direction moving mixer, subpackaging via a subpackaging machine according to 1.5 g per bottle, capping, labellling, and packaging to obtain sterile piperacillin sodium-sulbactam sodium powder injection for injection with mass ratio of 2:1 (calculated based on piperacillin and sulbactam), meeting national drug standard.

EXAMPLE 9

Preparation of Powder Injection with Piperacillin Sodium:Sulbactam Sodium at a Mass Ratio of 2:1

Formulation 4: 450 g of the cocrystal A of piperacillin sodium and sulbactam sodium, 600 g sulbactam sodium and 1200 g piperacillin sodium were prepared into 1000 units of powder injection.

The preparation method comprises: grinding the cocrystal A of piperacillin sodium and sulbactam sodium via a 80 mesh sieve, under 100-grade sterile room condition, adding sulbactam sodium and piperacillin sodium, mixing well by adopting a multi-direction moving mixer, subpackaging via a subpackaging machine according to 2.25 g per bottle, capping, labellling, and packaging to obtain sterile piperacillin sodium-sulbactam sodium powder injection for injection with mass ratio of 2:1 (calculated based on piperacillin and sulbactam), meeting national drug standard.

EXAMPLE 10

Respective content fluctuation range is obtained by dividing the maximal amounts of piperacillin sodium and sulbactam sodium which can fluctuate in the preparation formulation of Examples 6-9 by corresponding total amounts of piperacillin sodium and sulbactam sodium in the preparation respectively, and the value difference between extreme values is the upper- and lower-limit fluctuation range of the content ratio of them. Only the cocrystal was used in Example 6, and the ratio of piperacillin sodium and sulbactam sodium is fixed and cannot be changed, so the upper- and lower-limit fluctuation range is 0; and the change ranges of both ingredients in the commercial products are −10%-10%, the difference between the extreme values is 20%, and the results are shown in Table 6.

TABLE 6

Content ratio ranges of piperacillin sodium:sulbactam sodium in each preparation

| Preparation | Fluctuation range of piperacillin sodium | Fluctuation range of sulbactam sodium | Upper- and lower-limit range of content ratio fluctuation of piperacillin sodium:sulbactam sodium |
|---|---|---|---|
| Sample of Example 6 | 90%-110% | 90%-110% | 0 |
| Sample of Example 7 | 90%-110% | 90%-110% | 0.6% |
| Sample of Example 8 | 90%-110% | 90%-110% | 10.6% |
| Sample of Example 9 | 90%-110% | 90%-110% | 16% |
| Commercial piperacillin sodium-sulbactam sodium powder injection (2:1) | 90%-110% | 90%-110% | 20% |

It can be seen from the results of Table 6 that the preparations containing certain ratio (20-100%) of the cocrystal A of the present invention all can effectively reduce the fluctuation ranges of the piperacillin sodium:sulbactam sodium content ratios in the preparation products, greatly ensures the accuracy of administration amount, and provides further guarantee of effectiveness and safety of drugs.

EXAMPLE 11

The quality and stability of the powder injection samples of Examples 6, 7, 8 and 9 and commercial piperacillin sodium-sulbactam sodium powder injection (mass ratios are all 2:1) were tested. The stability test comprises: acceleration test under conditions of 40° C.±2° C. and RH 75%±5% for 6 months, and long-period stability test under conditions of 25° C.±2° C. and RH 60%+10% for 28 months. The experimental data results obtained are shown in Tables 7 and 8.

TABLE 7

Acceleration test results

| Time | Sample | Character | pH | Clarity (solubility) | Related substances (%) | Sulbactam sodium content (%) | Piperacillin sodium content (%) |
|---|---|---|---|---|---|---|---|
| 0 month | Sample of Example 6 | White powder | 5.8 | Meeting the requirements | 0.58 | 99.4 | 99.6 |
| | Sample of Example 7 | White powder | 5.8 | Meeting the requirements | 0.60 | 99.4 | 99.6 |
| | Sample of Example 8 | White powder | 5.9 | Meeting the requirements | 0.61 | 99.3 | 99.4 |
| | Sample of Example 9 | White powder | 5.9 | Meeting the requirements | 0.64 | 99.1 | 99.3 |
| | Commercial piperacillin sodium-sulbactam sodium powder injection | White powder | 5.9 | Meeting the requirements | 0.651 | 99.0 | 99.5 |
| 1 month | Sample of Example 6 | White powder | 5.9 | Meeting the requirements | 0.61 | 99.2 | 99.4 |
| | Sample of Example 7 | White powder | 5.9 | Meeting the requirements | 0.63 | 99.1 | 99.2 |
| | Sample of Example 8 | White powder | 5.9 | Meeting the requirements | 0.69 | 99.0 | 99.0 |
| | Sample of Example 9 | White powder | 5.9 | Meeting the requirements | 0.81 | 98.7 | 98.9 |
| | Commercial piperacillin sodium-sulbactam sodium powder injection | White powder | 5.6 | Meeting the requirements | 0.83 | 98.6 | 99.0 |
| 2 months | Sample of Example 6 | White powder | 6.0 | Meeting the requirements | 0.66 | 99.0 | 99.1 |
| | Sample of Example 7 | White powder | 5.9 | Meeting the requirements | 0.69 | 98.8 | 98.9 |
| | Sample of Example 8 | White powder | 6.0 | Meeting the requirements | 0.77 | 98.6 | 98.7 |
| | Sample of Example 9 | White powder | 5.5 | Meeting the requirements | 0.99 | 98.5 | 98.4 |
| | Commercial piperacillin sodium-sulbactam sodium powder injection | White powder | 5.4 | Meeting the requirements | 1.14 | 98.3 | 98.1 |
| 3 months | Sample of Example 6 | White powder | 5.8 | Meeting the requirements | 0.81 | 98.8 | 98.9 |
| | Sample of Example 7 | White powder | 5.9 | Meeting the requirements | 0.85 | 98.6 | 98.6 |
| | Sample of Example 8 | White powder | 5.6 | Meeting the requirements | 1.08 | 98.4 | 98.6 |
| | Sample of Example 9 | White powder | 5.5 | Meeting the requirements | 1.34 | 98.0 | 98.4 |
| | Commercial piperacillin sodium-sulbactam sodium powder injection | White powder | 5.3 | Meeting the requirements | 1.44 | 97.8 | 98.4 |
| 6 months | Sample of Example 6 | White powder | 5.8 | Meeting the requirements | 1.09 | 98.1 | 98.7 |
| | Sample of Example 7 | White powder | 5.8 | Meeting the requirements | 1.20 | 97.9 | 98.4 |
| | Sample of Example 8 | White powder | 5.7 | Meeting the requirements | 1.47 | 97.4 | 98.0 |
| | Sample of Example 9 | White powder | 5.3 | Meeting the requirements | 2.26 | 97.1 | 97.4 |
| | Commercial piperacillin sodium-sulbactam sodium powder injection | White powder | 5.1 | Meeting the requirements | 2.75 | 96.9 | 97.2 |

TABLE 8 long-period test results

| Time | Sample | Character | pH | Clarity (solubility) | Related substances (%) | Sulbactam sodium content (%) | Piperacillin sodium content (%) |
|---|---|---|---|---|---|---|---|
| 0 month | Sample of Example 6 | White powder | 5.8 | Meeting the requirements | 0.58 | 99.4 | 99.6 |
| | Sample of Example 7 | White powder | 5.9 | Meeting the requirements | 0.60 | 99.4 | 99.6 |
| | Sample of Example 8 | White powder | 5.8 | Meeting the requirements | 0.61 | 99.3 | 99.4 |
| | Sample of Example 9 | White powder | 5.7 | Meeting the requirements | 0.64 | 99.1 | 99.3 |
| | Commercial piperacillin sodium-sulbactam sodium powder injection | White powder | 5.9 | Meeting the requirements | 0.65 | 99.0 | 99.5 |
| 3 months | Sample of Example 6 | White powder | 5.9 | Meeting the requirements | 0.60 | 99.3 | 99.3 |
| | Sample of Example 7 | White powder | 5.8 | Meeting the requirements | 0.61 | 99.2 | 99.2 |
| | Sample of Example 8 | White powder | 5.9 | Meeting the requirements | 0.66 | 99.0 | 99.1 |
| | Sample of Example 9 | White powder | 5.7 | Meeting the requirements | 0.73 | 98.9 | 99.0 |
| | Commercial piperacillin sodium-sulbactam sodium powder injection | White powder | 5.6 | Meeting the requirements | 0.80 | 98.7 | 99.1 |
| 6 months | Sample of Example 6 | White powder | 5.7 | Meeting the requirements | 0.70 | 99.1 | 99.0 |
| | Sample of Example 7 | White powder | 5.8 | Meeting the requirements | 0.73 | 98.9 | 98.9 |
| | Sample of Example 8 | White powder | 5.9 | Meeting the requirements | 0.80 | 98.7 | 98.6 |
| | Sample of Example 9 | White powder | 5.8 | Meeting the requirements | 1.09 | 98.5 | 98.4 |
| | Commercial piperacillin sodium-sulbactam sodium powder injection | White powder | 5.6 | Meeting the requirements | 1.18 | 98.1 | 98.4 |
| 9 months | Sample of Example 6 | White powder | 5.8 | Meeting the requirements | 0.81 | 98.8 | 98.8 |
| | Sample of Example 7 | White powder | 5.8 | Meeting the requirements | 0.83 | 98.6 | 98.7 |
| | Sample of Example 8 | White powder | 5.9 | Meeting the requirements | 0.97 | 98.3 | 98.4 |
| | Sample of Example 9 | White powder | 5.7 | Meeting the requirements | 1.28 | 98.0 | 98.1 |
| | Commercial piperacillin sodium-sulbactam sodium powder injection | White powder | 5.6 | Meeting the requirements | 1.40 | 97.8 | 98.0 |
| 12 months | Sample of Example 6 | White powder | 6.0 | Meeting the requirements | 0.89 | 98.6 | 98.6 |
| | Sample of Example 7 | White powder | 5.7 | Meeting the requirements | 0.90 | 98.4 | 98.4 |
| | Sample of Example 8 | White powder | 5.9 | Meeting the requirements | 1.15 | 98.0 | 98.1 |
| | Sample of Example 9 | White powder | 5.6 | Meeting the requirements | 1.56 | 97.7 | 97.8 |
| | Commercial piperacillin sodium-sulbactam sodium powder injection | White powder | 5.5 | Meeting the requirements | 1.71 | 97.6 | 97.7 |
| 18 months | Sample of Example 6 | White powder | 5.9 | Meeting the requirements | 1.02 | 98.3 | 98.3 |
| | Sample of Example 7 | White powder | 5.8 | Meeting the requirements | 1.06 | 98.1 | 98.2 |
| | Sample of Example 8 | White powder | 5.7 | Meeting the requirements | 1.57 | 97.6 | 97.7 |
| | Sample of Example 9 | White powder | 5.5 | Meeting the requirements | 2.05 | 97.2 | 97.4 |
| | Commercial piperacillin sodium-sulbactam sodium powder injection | White powder | 5.4 | Meeting the requirements | 2.32 | 97.1 | 97.3 |

TABLE 8-continued long-period test results

| Time | Sample | Character | pH | Clarity (solubility) | Related substances (%) | Sulbactam sodium content (%) | Piperacillin sodium content (%) |
|---|---|---|---|---|---|---|---|
| 24 months | Sample of Example 6 | White powder | 6.0 | Meeting the requirements | 1.17 | 98.0 | 98.1 |
| | Sample of Example 7 | White powder | 5.8 | Meeting the requirements | 1.20 | 97.9 | 98.0 |
| | Sample of Example 8 | White powder | 5.7 | Meeting the requirements | 1.86 | 97.3 | 97.4 |
| | Sample of Example 9 | White powder | 5.3 | Meeting the requirements | 2.49 | 97.0 | 96.9 |
| | Commercial piperacillin sodium-sulbactam sodium powder injection | White powder | 5.2 | Meeting the requirements | 2.78 | 96.9 | 96.8 |
| 28 months | Sample of Example 6 | White powder | 5.7 | Meeting the requirements | 1.30 | 97.6 | 97.9 |
| | Sample of Example 7 | White powder | 5.7 | Meeting the requirements | 1.38 | 97.3 | 97.7 |
| | Sample of Example 8 | White powder | 5.5 | Meeting the requirements | 2.05 | 96.8 | 97.1 |
| | Sample of Example 9 | White powder | 5.2 | Meeting the requirements | 2.99 | 96.5 | 96.6 |
| | Commercial piperacillin sodium-sulbactam sodium powder injection | White powder | 4.9 | Meeting the requirements | 3.26 | 96.3 | 96.4 |

It can be seen from the data of Tables 7-8 above that: the stability of the preparations of Examples 6, 7 and 8 of the present invention is better than that of commercial piperacillin sodium-sulbactam sodium powder injection (2:1), while the preparation of Example 9 is slightly better than the commercial product, but there is no significant difference. After accelerating for 6 months and for a long period of 28 months, the quality indexes of the samples of Examples 6, 7 and 8 of the present invention all have no significant change, and all meet the quality standard requirements, while the indexes of the sample of Example 9 under same conditions obviously changes, and is almost unqualified. Similarly, under the acceleration and long-period test conditions, the commercial piperacillin sodium-sulbactam sodium powder injection (2:1) has obvious changes such as impurity increase and content decrease, and during the 28th month, the commercial piperacillin sodium-sulbactam sodium powder injection (2:1) has become unqualified sample due to excessive level of related substances.

The above-mentioned acceleration and long-period stability tests sufficiently show that the product quality of piperacillin sodium-sulbactam sodium product quality for injection produced using the cocrystal A of the present invention as raw material is more stable, and more suitable for drug industrial production.

EXAMPLE 12

Determination of Antibacterial Activity

Samples of the preparations of Examples 6 and 8 were determined for antibacterial activity.

The method for determination comprises: diluting samples of the preparations of Examples 6 and 8 and commercial piperacillin sodium-sulbactam sodium powder injection (2:1) to 512 mg/l with distilled water, providing 15 test tubes while testing each sample, and additionally providing 2 test tubes as positive control and negative control, adding MH broth 1 ml into each test tube, adding 1 ml of the sample diluted to 512 mg/l with distilled water into the first test tube, mixing well, extracting 1 ml into the second test tube, sequentially diluting 2 times into the tenth test tube, extracting 1 ml, and discarding. By this time, sample concentrations in each test tube are 256 mg/l, 128 mg/l, 64 mg/l, 32 mg/l, 16 mg/l, 8 mg/l, 4 mg/l, 2 mg/l, 1 mg/l and 0.5 mg/l respectively.

NDM-1-producing NS-91 (*Klebsiella pneumoniae*) and NS-96 (*Escherichia coli*) were obtained from clinical isolation, and ATCC25922 (*Escherichia coli*) was purchased from ATCC. The strains were firstly calibrated with normal saline to 0.5 Mcfarland turbidity concentration, followed by diluting with MH broth according to 1:10 (bacterium content is about $10^7$CFU/mL), adding diluted strain solution 50 ul into each tube and positive control tube respectively (50 ul per tube) to the final strain solution concentration of $5 \times 10^5$ CFU/mL, capping with a test tube plug after inoculating, placing in a 37° C. constant temperature incubator overnight, and determining minimal inhibitory concentration (MIC). The results are shown in Table 9:

TABLE 9

Inhibition effect of each sample on 3 clinically-isolated strains (MIC, mg/L)

| | Strain (MIC) | | |
|---|---|---|---|
| Sample | NS-91 (*Klebsiella pneumoniae*) | NS-96 (*Escherichia coli*) | ATCC25922 *Escherichia coli* |
| Sample of Example 6 | 1 | 2 | 0.5 |
| Sample of Example 8 | 1 | 2 | 0.5 |
| Commercial piperacillin sodium-sulbactam sodium powder injection | 1 | 2 | 0.5 |

It can be seen from the Table above that: the preparations of Examples 6 and 8 can effectively inhibit NDM-1-producing "super bacterium", and can be used for treating injections caused by drug-resistant bacteria such as NDM-1-producing "super bacterium" and the like. The preparations of Examples 7 and 9 were subjected to same experiment, and similar effect was obtained.

It was shown that the piperacillin sodium-sulbactam sodium products for injection produced using the cocrystal A of the present invention as raw material have stable curative effect, and can replace and are better than commercial products.

INDUSTRIAL APPLICABILITY

The pharmaceutical compositions containing the cocrystal of piperacillin sodium and sulbactam sodium of the present invention have antibacterial effect, especially have obvious therapeutic effect on infections caused by NDM-1 drug-resistant bacteria.

What is claimed is:

1. A cocrystal of piperacillin sodium and sulbactam sodium, comprising diffraction angles of 14.24°, 16.58°, 16.79°, 17.77°, 19.20°, 20.21°, 20.39°, 23.06°, 27.86° and 32.16° represented by 2θ in an X-ray powder diffraction analysis spectrum.

2. The cocrystal according to claim 1, characterized in that, in the X-ray powder diffraction analysis spectrum, the parameters of the cocrystal, viz. interplanar crystal spacing d(Å), diffraction peak height relative intensity $I/I_0$ and 2θ diffraction angle, are expressed as $d/I/I_0/2θ$ and include: 6.21/100.0/14.24, 5.34/28.5/16.58, 5.27/10.6/16.79, 4.98/12.9/17.77, 4.61/29.0/19.20, 4.39/22.2/20.21, 4.35/17.4/20.39, 3.85/7.9/23.06, 3.20/18.6/27.86, and 2.78/8.2/32.16.

3. The cocrystal according to claim 2, characterized in that, $d/I/I_0/2θ$ include: 6.21/100.0/14.24, 5.34/28.5/16.58, 5.27/10.6/16.79, 5.05/4.2/17.53, 4.98/12.9/17.76, 4.83/3.4/18.36, 4.61/29.0/19.20, 4.39/22.2/20.21, 4.35/17.4/20.39, 3.85/7.9/23.06, 3.61/4.0/24.58, 3.56/5.2/24.96, 3.20/18.6/27.85, 3.09/4.5/28.78, 2.90/3.0/30.77, 2.84/4.2/31.42, 2.78/8.2/32.16, 2.66/3.8/33.65, 2.57/2.9/34.85, 2.49/5.8/35.93, 2.34/4.6/38.31, and 2.31/3.8/38.82.

4. The cocrystal according to claim 1, characterized in that, in a differential scanning calorimetry analysis spectrum, it has exothermic peaks at 192.2° C. and 287.9° C.

5. The cocrystal according to claim 1, characterized in that, in an infrared absorption spectrum, it has absorption peaks at 3437 $cm^{-1}$, 2976 $cm^{-1}$, 1774 $cm^{-1}$, 1715 $cm^{-1}$, 1676 $cm^{-1}$, 1607 $cm^{-1}$, 1520 $cm^{-1}$, 1464 $cm^{-1}$, 1398 $cm^{-1}$, 1304 $cm^{-1}$, 1196 $cm^{-1}$, 1124 $cm^{-1}$, 1090 $cm^{-4}$, 1013 $cm^{-1}$, 949 $cm^{-1}$, 897 $cm^{-1}$, 750 $cm^{-1}$, 704 $cm^{-1}$, 600 $cm^{-1}$.

6. The cocrystal according to claim 1, characterized in that, the molar ratio of piperacillin sodium to sulbactam sodium in the cocrystal is 1:1.

7. A method for preparation of the cocrystal according to claim 1, comprising: adding piperacillin sodium and sulbactam sodium into a mixture solution 1 of ketone, dimethylformamide and water, adding ketone 1 and filtering off insoluble substances; then standing at 2-10° C. for 20-30 h, and filtering off resulted crystals; and sequentially washing the filtered crystals with a mixture solution 2 of ketone, dimethylformamide and water and ketone 2 to obtain the cocrystal.

8. The method according to claim 7, characterized in that, the ketones are all selected from one or more of propiophenone, 2-pentanone, butanone and acetone.

9. The method according to claim 7, characterized in that, the molar ratio of piperacillin sodium to sulbactam sodium is 2:1-1:2.

10. The method according to claim 7, characterized in that, after filtering off insoluble substances, the temperature for standing is 5° C., and the standing time is 24 h.

11. The method according to claim 7, characterized in that, the volume ratio of ketone, dimethylformamide and water in the mixture solution 1 is (40-50):(30-35):12; and the volume ratio of ketone, dimethylformamide and water in the mixture solution 2 is (720-800):(60-68):(20-24).

12. The method according to claim 7, characterized in that, the mass-to-volume ratio of piperacillin sodium to the mixture solution 1 is (40-42):(82-97).

13. The method according to claim 7, characterized in that, the mass-to-volume ratio of piperacillin sodium to ketone 1 is (40-42):(280-300).

14. A pharmaceutical composition containing the cocrystal according to claim 1, wherein 1-100% by weight percentage of the pharmaceutical composition is the cocrystal of piperacillin sodium and sulbactam sodium.

15. The pharmaceutical composition according to claim 14, characterized in that, 0-80% by weight percentage of the pharmaceutical composition is piperacillin sodium and/or sulbactam sodium.

16. The pharmaceutical composition according to claim 14, characterized in that, the mass ratio of piperacillin sodium to sulbactam sodium in the pharmaceutical composition is 2:1.

17. The pharmaceutical composition according to claim 14, characterized in that, the pharmaceutical composition is prepared into injection.

18. A method of treating an infection caused by bacteria comprising applying to the infection the pharmaceutical composition according to claim 14.

19. The method according to claim 18 wherein the infection is caused by NDM-1-producing drug-resistant bacteria.

* * * * *